United States Patent [19]

Murata et al.

[11] Patent Number: 5,100,908
[45] Date of Patent: Mar. 31, 1992

[54] ANTIMYCOTIC EXTERNAL IMIDAZOLE PREPARATIONS

[75] Inventors: Yutaka Murata, Yachiyo; Takashi Narui, Sakura; Tetsuo Kaneko; Takemitsu Asaoka, both of Narita; Katsumi Imamori; Akira Iwasa, both of Yotsukaido, all of Japan

[73] Assignee: SS Pharmaceutical Co., Ltd., Tokyo, Japan

[21] Appl. No.: 650,969

[22] Filed: Feb. 5, 1991

[30] Foreign Application Priority Data

Mar. 6, 1990 [JP] Japan ............... 2-54447
Mar. 6, 1990 [JP] Japan ............... 2-54448
Mar. 6, 1990 [JP] Japan ............... 2-54449

[51] Int. Cl.$^5$ ............................ A61K 31/415
[52] U.S. Cl. ............................ 514/396
[58] Field of Search ................. 514/396

[56] References Cited

U.S. PATENT DOCUMENTS

| | | | |
|---|---|---|---|
| 3,660,577 | 5/1972 | Buchel et al. | 514/396 |
| 4,237,158 | 12/1980 | Miller et al. | 424/273 R |
| 4,238,498 | 12/1980 | Regel et al. | 424/273 R |
| 4,740,601 | 4/1988 | Ogawa et al. | 548/336 |
| 4,782,053 | 11/1988 | Pettman et al. | 514/231.2 |
| 4,897,427 | 1/1990 | Barnavon et al. | 514/396 |
| 4,914,120 | 4/1990 | Wilson | 514/400 |

FOREIGN PATENT DOCUMENTS

| | | |
|---|---|---|
| 0170139 | 2/1986 | European Pat. Off. . |
| 0227011 | 7/1987 | European Pat. Off. . |
| 0310122 | 4/1989 | European Pat. Off. . |
| 2619311 | 2/1989 | France . |

OTHER PUBLICATIONS

Chemotherapy, vol. 38, No. 8, Aug. 1990, pp. 769-779, Tokyo, JP; H Yamaue et al.: "In vitro antitumor activity of a new platinum analogue, NK 12 against fresh human tumor cell lines by succinate dehydrogenase inhibition test" p. 779 summary.

Ogawa et al. 1988, Chem. Abs, 108(1): Prep'n of (phenyl ethenyl) imidazoles as bactericides & fungicides.

Primary Examiner—S. J. Friedman
Attorney, Agent, or Firm—Oblon, Spivak, McClelland, Maier & Neustadt

[57] ABSTRACT

Antimycotic external imidazole preparations are disclosed. They contain the following ingredients:
 (a) 0.1-5 wt. % of (E)-1-[2-methylthio-1-[2-(pentyloxy)phenyl]ethenyl]-1H-imidazole hydrochloride;
 (b) 0.01-3 wt. % of a basic substance; and
 (c) an external preparation base.

7 Claims, 3 Drawing Sheets

ANTIMYCOTIC EXTERNAL IMIDAZOLE PREPARATIONS

BACKGROUND OF THE INVENTION

1) Field of the Invention

This invention relates to novel antimycotic external imidazole preparations, and more specifically to external preparations which have reduced skin irritation, can show their effects to maximum extent and over a prolonged period of time and are physicochemically stable.

2) Description of the Related Art

Antimycotic imidazole preparations having antifungal activities against fungi and the like have already been marketed with preparation forms such as cream preparations, gel preparations and liquid preparations owing to their merits such that they have a broad antifungal spectrum and fewer resistant fungi occur clinically.

These conventional, commercial antimycotic imidazole preparations are however not fully satisfactory, because they are accompanied by drawbacks such as skin irritation and/or poor stability.

For example, liquid preparations often contain an alcohol, leading to the drawback that they have skin irritation due to the alcohol. Gel preparations also contain an alcohol or the like while cream preparations contain an emulsifier and a preservative, so that they also have the problem of skin irritation.

It is required to enhance antifungal activities so that the period of treatment can be shortened and the frequency of application can be reduced. To achieve this, it is necessary to design a base such that the effectiveness can be optimized in the treatment, for example, by improving spreadability, maintaining good releasability and enhancing retaining effects. No external preparation capable of meeting these requirements has however yet been provided.

It has hence been desired to provide an antimycotic external preparation which has low skin irritation and can fully exhibit excellent effects.

SUMMARY OF THE INVENTION

With the foregoing in view, the present inventors have proceeded with an extensive investigation. As a result, it has been found that an external preparation which is obtained by mixing (E)-1-[2-methylthio-1-[2-(pentyloxy)phenyl]ethenyl]-1H-imidazole hydrochloride, active ingredient, and a basic substance in combination an external preparation base - has low skin irritation, can continuously exhibit curative effects and is physicochemically stable, leading to the completion of the present invention.

Namely, the present invention provides an antimycotic external imidazole preparation comprising the following ingredients:

(a) 0.1–5 wt. % of (E)-1-[2-methylthio-1-[2-(pentyloxy)phenyl]ethenyl]-1H-imidazole hydrochloride;
(b) 0.01–3 wt. % of a basic substance; and
(c) an external preparation base.

Each external preparation of the present invention shows excellent pharmacological effects since (E)-1-[2-methylthio-1-[2-(pentyloxy)phenyl]ethyl]-1H-imidazole hydrochloride, the active ingredient (a), and the basic substance act synergistically and its corresponding external preparation base is combined.

When formed as external liquid preparations, they have excellent affinity with and spreadability on the skin, enhance the activities of their active ingredient and control the release of the active ingredients. Accordingly, the retainability on the skin is enhanced and curative effects can be exhibited over a prolonged period of time. Further, skin irritation is reduced.

When formed as ointment preparations, the active ingredient is dissolved to suitable extent in the base and the release of the active ingredient is controlled by the addition of the liquid oil substance. The retainability on the skin is therefore enhanced and curative effects can be exhibited over a prolonged period of time.

Further, cream preparations can control the releasability of the active ingredient, have enhanced retainability on the skin and can exhibit curative effects over a prolonged period of time, because the activities of the active ingredient are enhanced and the active ingredient is dissolved to suitable degree in the base. By the addition of a liquid oil substance, the preparations are rendered excellent not only in spreadability and percutaneous absorption but also in physicochemical stability, and their skin irritation is reduced.

The antimycotic external imidazole preparations of the present invention have reduced skin irritation, give good feeling upon use, can exhibit superb curative effects over a prolonged period of time, and are physicochemically stable. They are therefore extremely advantageous as external antimycotic preparations for the skin or the like.

DETAILED DESCRIPTION OF THE INVENTION AND PREFERRED EMBODIMENTS

Figure 1:
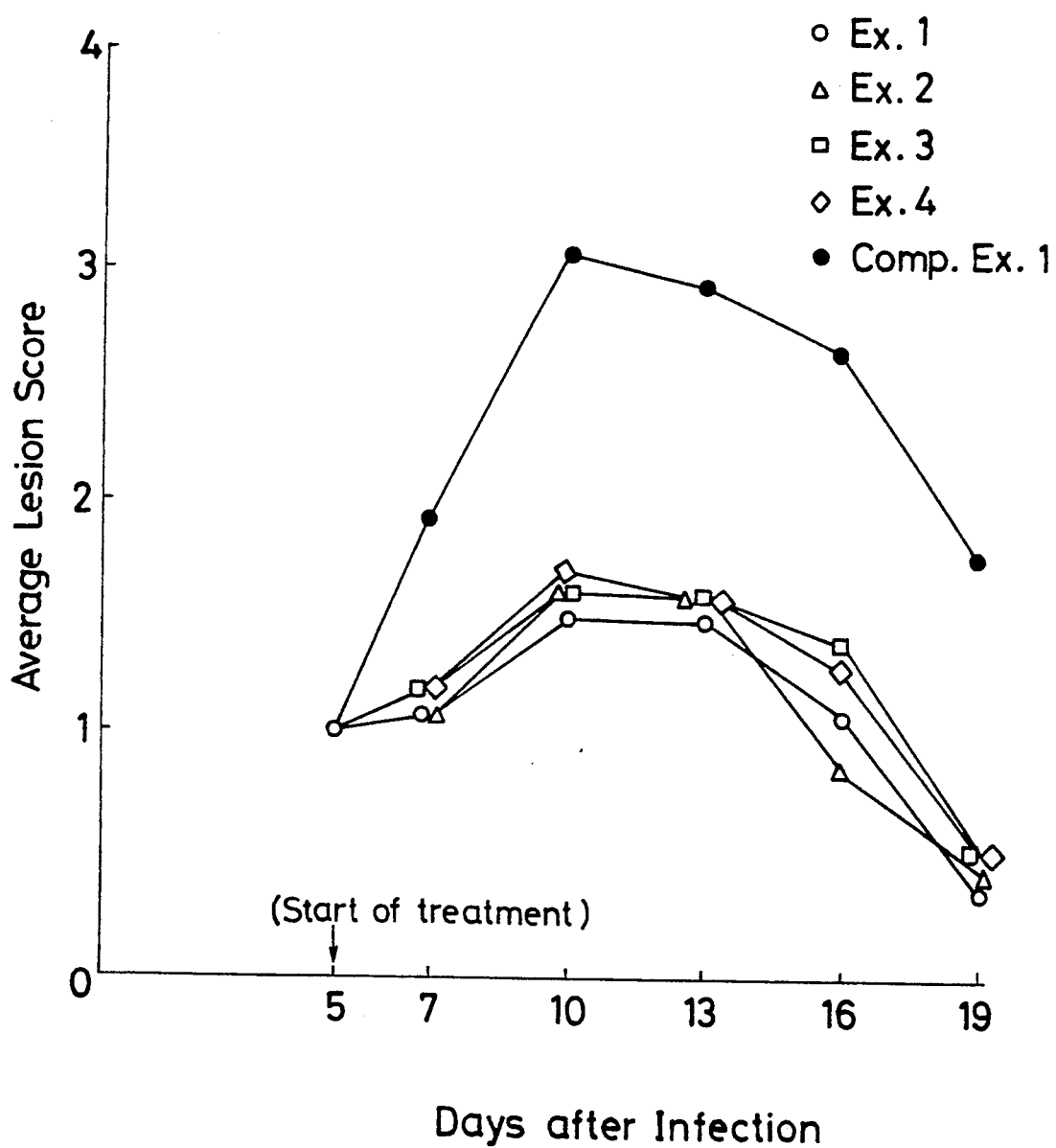
FIG. 1 diagrammatically shows the results of the effectiveness test conducted in Test 1 with respect to the external liquid preparations of the present invention, which illustrates their effectiveness in terms of average lesion score vs. days after infection.

The term "external preparation" as used herein embraces preparations generally applied to skin surfaces such as external liquid preparations, ointment preparations and cream preparations.

(E)-1-[2-methylthio-1-[2-(pentyloxy)phenyl]-ethenyl]-1H-imidazole hydrochloride (hereinafter called "Compound A"), ingredient (a), i.e., the active ingredient in the external preparation of this invention is a known substance having excellent antibacterial activities against bacteria, fungi and the like (Japanese Patent Application Laid-Open No. 146864/1988). Compound A is added in a proportion of 0.1–5 wt. % (hereinafter indicated merely by "%"), preferably 0.5–1.5% based on the whole composition.

On the other hand, examples of the basic substance as ingredient (b) include organic amines such as alkylamines and mono-, di- and trialkanolamines; and inorganic alkalis such as alkali hydroxides and alkali carbonates. Among these, monoethanolamine, diethanolamine, triethanolamine, sodium hydroxide, potassium hydroxide and the like are particularly preferred. Ingredient (b) is added in a proportion of 0.01-3%, preferably 0.1-1% based on the whole composition.

The external preparation base as ingredient (c) can be suitably selected in accordance with the preparation form of the intended external preparation in the present invention.

To prepare an external preparation in the form of an external liquid preparation, it is preferable to use, as a base, a liquid preparation base which contains a nonionic surfactant and a liquid oil substance in proportions of 1-25% and 1-55%, respectively based on the whole composition. As the nonionic surfactant contained in the above liquid preparation base, a polyoxyalkylene ester or ether surfactant is preferred, with an ester-type surfactant between polyoxyethylene (POE) and a saturated fatty acid or an ether-type surfactant between POE and a saturated aliphatic alcohol being particularly preferred. Specific examples include POE monolaurate, POE monostearate, POE lauryl ether, POE cetyl ether, POE hydrogenated castor oil and the like. They can be added preferably in a proportion of 2-15% based on the whole composition. No particular limitation is imposed on the liquid oil substance insofar as it is liquid at room temperature. Particularly preferred are fatty acid esters, including diisopropyl adipate, diethyl sebacate and isopropyl myristate by way of example. They can be used either singly or in combination. They can be added preferably in a proportion of 5-45% based on the whole composition. Further, the external liquid preparation base can also be added with ethanol in a proportion of 5-80%, preferably 30-70% based on the whole composition. Further addition of purified water is preferred.

To prepare an external preparation in the form of an ointment preparation, it is preferable to use, as a base, an ointment base which contains a nonionic surfactant and an oleaginous ointment base in proportions of 2-5% and at least 80%, respectively based on the whole composition. As the nonionic surfactant which is contained in the above base, a polyoxyalkylene alkyl ether, polyalkylenelycol fatty acid ester, polyoxyalkylene hydrogenated castor oil, sorbitan fatty acid ester, propyleneglycol fatty acid ester or the like can be used. Specific examples include POE oleyl ether, POE monolaurate, POE hydrogenated castor oil 5, sorbitan sesquioleate, and propyleneglycol monostearate. They can be added preferably in a proportion of 2.5-3.5% based on the whole composition. On the other hand, as the oleaginous ointment base, it is preferable to use (i) a mineral oil, for example, yellow soft paraffin, white soft paraffin, paraffin, liquid paraffin, plastibase, ZELEN 50W or silicone in combination with (ii) a liquid oil substance selected from diethyl sebacate, diisopropyl adipate, medium-chain fatty acid triglycerides and 2-octyldodecanol. These oleaginous ointment bases can be added preferably in an amount of 90-95%. Of these components, the liquid oil substance (ii) can be added preferably in a proportion of 2-15%, notably 5-10% based on the whole composition. Further, the ointment base can also be added with water in a proportion of 1-10%, preferably 2-5% based on the whole composition. In addition, it is also preferable to use, as a stabilizer, butylhydroxyanisole or dibutylhydroxytoluene (BHT) in combination with disodium edetate.

To prepare the external preparation of this invention in the form of a cream preparation, it is preferable to use a cream base which contains a nonionic surfactant, an oil substance and water in proportions of 1-20%, 2-50% and 40-90%, respectively based on the whole composition.

Exemplary nonionic surfactants which can be contained in the above cream base include polyoxyalkylene surfactants such as polyoxyalkylene sorbitan fatty acid esters, polyoxyalkylene alkyl ethers, polyoxyalkyleneglycol fatty acid esters and polyoxyalkylene hydrogenated castor oil; and fatty acid ester surfactants such as sorbitan fatty acid esters and glycerin fatty acid esters. Specific examples include sorbitan monostearate, POE sorbitan monostearate, glyceryl monostearate, POE cetyl ether, polyethyleneglycol monostearate, and POE hydrogenated castor oil. They can be added preferably in a proportion of 2-10% based on the whole composition.

No particular limitation is imposed on the oil substance insofar as it can be used in general cream preparations. Usable exemplary oil substances include hydrocarbons such as light liquid paraffin, squalane, white soft paraffin, microcrystalline wax and ceresin; waxes such as beeswax, spermaceti and carnauba wax; fatty acid esters such as diethyl sebacate, diisopropyl adipate, cetyl lactate, cetyl palmitate and myristyl myristate; aliphatic alcohols such as stearyl alcohol, 2-octyldodecanol, 2-hexyldecanol and cetanol; triglycerides such as natural fatty acid triglyceride and medium-chain fatty acid triglycerides; fatty acids such as palmitic acid, stearic acid and myristic acid; etc. Among these, as to aliphatic compounds, saturated aliphatic compounds are particularly preferred. Described specifically, stearyl alcohol, white soft paraffin, medium-chain fatty acid triglycerides, diethyl sebacate, octyldodecanol and squalane are particularly preferred. They can be used either singly or in combination. They can be added preferably in a proportion of 10-30% based on the whole composition. Further, water can also be added preferably in a proportion of 60-80%.

The external preparations of the present invention can each be produced by adding the above three ingredients by a conventional method suited for the preparation form. To extent not impairing the effects of the present invention, the external preparations of the present invention can be added with various conventional additives, for example, stabilizers, perfumes, colorants, suspending agents, etc. In particular, to prepare an external preparation in the form of a cream preparation, it is desirable to add one or more conventional stabilizers, for example, an antioxidant such as butylhydroxyanisole, dibutylhydroxytoluene or propyl gallate; an antiseptic such as a paraoxybenzoic acid ester or dehydroacetic acid; and/or a chelating agent such as disodium edetate or tetrasodium edetate.

The present invention will hereinafter be described in further detail by the following examples, comparative examples and tests. It should be borne in mind however that the present invention is not limited whatsoever to or by the following examples.

EXAMPLE 1

| | |
|---|---|
| Compound A | 1 g |
| Diethyl sebacate | 15 g |
| POE (10) monolaurate | 5 g |
| Triethanolamine | 0.465 g |
| Ethanol | 56 g |

After Compound A was dissolved in ethanol, diethyl sebacate and POE(10) monolaurate were mixed. Added next was a solution of triethanolamine in a suitable amount of purified water. Purified water was then added in an amount sufficient to produce 100 ml, whereby an external liquid preparation was obtained.

EXAMPLE 2

| | |
|---|---|
| Compound A | 1 g |
| Diethyl sebacate | 30 g |
| Diisopropyl adipate | 10 g |
| POE (5.5) cetyl ether | 5 g |
| Triethanolamine | 0.465 g |
| Ethanol | 35 g |
| Purified water | q.s. to 100 ml. |

An external liquid preparation was prepared in a similar manner to Example 1.

Example 3

| | |
|---|---|
| Compound A | 1 g |
| Diethyl sebacate | 30 g |
| POE (60) hydrogenated castor oil | 5 g |
| Sodium hydroxide | 0.115 g |
| Ethanol | 42 g |
| Purified water | q.s. to 100 ml. |

An external liquid preparation was prepared in a similar manner to Example 1.

EXAMPLE 4

| | |
|---|---|
| Compound A | 1 g |
| Isopropyl myristate | 10 g |
| POE (10) monolaurate | 10 g |
| Triethanolamine | 0.465 g |
| Ethanol | 56 g |
| Purified water | q.s. to 100 ml. |

An external liquid preparation was prepared in a similar manner to Example 1.

COMPARATIVE EXAMPLE 1

| | |
|---|---|
| Compound A | 1 g |
| Diethyl sebacate | 30 g |
| POE (10) monooleate | 5 g |
| Ethanol | 42 g |
| Purified water | q.s. to 100 ml. |

An external liquid preparation was prepared in a similar manner to Example 1.

EXAMPLE 5

| | |
|---|---|
| Compound A | 1 g |
| Diethyl sebacate | 5 g |
| POE (5) hydrogenated castor oil | 3 g |
| Sodium hydroxide | 0.14 g |
| Purified water | 3.86 g |
| BH | 0.05 g |
| Disodium edetate | 0.05 g |
| White soft paraffin | 86.9 g |

White soft paraffin was melted at 70°-80° C., in which BHT was dissolved. The other ingredients which had been mixed at room temperature on the side were then added. The resulting mixture was stirred at 60-70° C. and then allowed to cool down to 45° C. as it was, whereby an ointment preparation was obtained.

EXAMPLE 6

| | |
|---|---|
| Compound A | 1 g |
| Diisopropyl adipate | 5 g |
| Sorbitan sesquioleate | 3 g |
| Triethanolamine | 0.44 g |
| Purified water | 2.56 g |
| BHT | 0.05 g |
| Disodium edetate | 0.05 g |
| White soft paraffin | 87.9 g |

An ointment preparation was obtained in a similar manner to Example 5.

EXAMPLE 7

| | |
|---|---|
| Compound A | 1 g |
| Medium-chain fatty acid triglyceride | 10 g |
| Sorbitan sesquioleate | 3 g |
| Diethanolamine | 0.32 g |
| Purified water | 2.68 g |
| BHT | 0.05 g |
| Disodium edetate | 0.05 g |
| White soft paraffin | 82.9 g |

An ointment preparation was obtained in a similar manner to Example 5.

EXAMPLE 8

| | |
|---|---|
| Compound A | 1 g |
| 2-Octyldodecanol | 10 g |
| Sorbitan sesquioleate | 3 g |
| Potassium hydroxide | 0.16 g |
| Purified water | 2.84 g |
| BHT | 0.05 g |
| Disodium edetate | 0.05 g |
| White soft paraffin | 82.9 g |

An ointment preparation was obtained in a similar manner to Example 5.

COMPARATIVE EXAMPLE 2

| | |
|---|---|
| Compound A | 1 g |
| Diethyl sebacate | 5 g |
| Lauromacrogol | 3 g |
| Sodium hydroxide | 0.12 g |
| Purified water | 3.17 g |
| BHT | 0.02 g |
| Disodium edetate | 0.02 g |
| Japanese Pharmacopoeia macrogol ointment | 87.67 g |

Japanese Pharmacopoeia macrogol ointment was molten at 70°-80° C., to which lauromacrogol was added BHT, disodium edetate and diethyl sebacate were added further, followed by stirring. Compound A was then added. The resultant mixture was stirred and was then allowed to cool down to 40° C. as it was, whereby an ointment preparation was obtained.

COMPARATIVE EXAMPLE 3

| | |
|---|---|
| Compound A | 1 g |
| Diethyl sebacate | 5 g |
| Cetyl lactate | 2 g |
| Lauromacrogol | 3 g |
| Sodium hydroxide | 0.14 g |
| Purified water | 3.46 g |
| BHT | 0.05 g |
| Disodium edetate | 0.05 g |
| Japanese Pharmacopoeia macrogol ointment | 85.3 g |

An ointment preparation was obtained in a similar manner to Comparative Example 2.

COMPARATIVE EXAMPLE 4

| | |
|---|---|
| Compound A | 1 g |
| Diethyl sebacate | 5 g |
| Propylene glycol | 3 g |
| Lauromacrogol | 3 g |
| Diethanolamine | 0.32 g |
| Purified water | 2.68 g |
| Japanese Pharmacopoeia macrogol ointment | 85 g |

An ointment preparation was obtained in a similar manner to Comparative Example 2.

COMPARATIVE EXAMPLE 5

| | |
|---|---|
| Compound A | 1 g |
| Diethyl sebacate | 5 g |
| Sorbitan sesquioleate | 3 g |
| Purified water | 3 g |
| BHT | 0.05 g |
| Disodium edetate | 0.05 g |
| White soft paraffin | 87.9 g |

An ointment preparation was obtained in a similar manner to Comparative Example 2.

EXAMPLE 9

| | |
|---|---|
| Compound A | 1.0 g |
| Stearyl alcohol | 4.0 g |
| White soft paraffin | 5.0 g |
| Medium-chain fatty acid triglyceride | 12.0 g |
| Glyceryl monostearate | 3.0 g |
| POE (25) cetyl ether | 2.0 g |
| Methyl paraoxybenzoate | 0.2 g |
| Butyl paraoxybenzoate | 0.1 g |
| Disodium edetate | 0.02 g |
| Triethanolamine | 0.465 g |
| Purified water | q.s. to 100 g |

The oil-phase ingredients were melted at 60°–70° C., to which Compound A dissolved in a portion of purified water was added under stirring. An aqueous solution of the other ingredients in the remaining portion of the purified water was added. The resulting mixture was emulsified at 70°–75° C. and then allowed to cool down to room temperature, whereby a cream preparation was obtained.

EXAMPLE 10

| | |
|---|---|
| Compound A | 1.0 g |
| Cetanol | 5.0 g |
| White soft paraffin | 6.0 g |
| Diethyl sebacate | 12.0 g |
| Glyceryl monostearate | 4.0 g |
| POE (25) cetyl ether | 2.0 g |
| Methyl paraoxybenzoate | 0.2 g |
| Butyl paraoxybenzoate | 0.1 g |
| Disodium edetate | 0.02 g |
| Triethanolamine | 0.465 g |
| Purified water | q.s. to 100 g | manner to Example 9.

EXAMPLE 11

| | |
|---|---|
| Compound A | 1.0 g |
| Stearyl alcohol | 4.0 g |
| White soft paraffin | 5.0 g |
| 2-Octyldodecanol | 15.0 g |
| Sorbitan monostearate | 2.0 g |
| POE (20) sorbitan monostearate | 3.0 g |
| Methyl paraoxybenzoate | 0.2 g |
| Butyl paraoxybenzoate | 0.1 g |
| Disodium edetate | 0.02 g |
| Sodium hydroxide | 0.115 g |
| Purified water | q.s. to 100 g |

A cream preparation was prepared in a similar manner to Example 9.

EXAMPLE 12

| | |
|---|---|
| Compound A | 1.0 g |
| Cetanol | 5.0 g |
| White soft paraffin | 6.0 g |
| White beeswax | 2.0 g |
| Squalane | 10.0 g |
| Glyceryl monostearate | 3.2 g |
| POE (25) cetyl ether | 1.8 g |
| Methyl paraoxybenzoate | 0.2 g |
| Butyl paraoxybenzoate | 0.1 g |
| Disodium edetate | 0.02 g |
| Triethanolamine | 0.465 g |
| Purified water | q.s. to 100 g |

A cream preparation was prepared in a similar manner to Example 9.

EXAMPLE 13

| | |
|---|---|
| Compound A | 1.0 g |
| Cetanol | 5.0 g |
| White soft paraffin | 6.0 g |
| Medium-chain fatty acid triglyceride | 10.0 g |
| Diethyl sebacate | 5.0 g |
| Glyceryl monostearate | 4.0 g |
| POE (25) cetyl ether | 2.0 g |
| Methyl paraoxybenzoate | 0.2 g |
| Butyl paraoxybenzoate | 0.1 g |
| Disodium edetate | 0.02 g |
| Triethanolamine | 0.465 g |
| Purified water | q.s. to 100 g |

A cream preparation was prepared in a similar manner to Example 9.

COMPARATIVE EXAMPLE 6

| | |
|---|---|
| Compound A | 1.0 g |
| Stearyl alcohol | 4.0 g |
| White soft paraffin | 5.0 g |
| Oleic acid | 10.0 g |
| Glyceryl monostearate | 3.0 g |
| POE (25) cetyl ether | 2.0 g |

| -continued | |
|---|---|
| Methyl paraoxybenzoate | 0.2 g |
| Butyl paraoxybenzoate | 0.1 g |
| Propylene glycol | 5.0 g |
| Disodium edetate | 0.02 g |
| Purified water | q.s. to 100 g |

A cream preparation was prepared in a similar manner to Example 9.

Test 1 (Effectiveness Test)

A Trichophyton infection treatment test of certain external preparations according to this invention was conducted by the following method:

Hair was pulled out at four parts on the back of each guinea pig. Those parts were infected with a culture of *Trichophyton mentagrophyres* TIMM 1189 strain. From the fifth day after the infection to the fungus, a test preparation was applied once a day for straight 14 days. The lesion score was ranked in accordance with the following standard. The smaller the lesion score, the higher the effectiveness.

+1: A small number of tiny erythema and/or erythematous papule are observed in a state scattered like isles, or the lesion is convalescing and new body hair has been growing.

+2: Erythema has spread all over the infected parts with separation of epidermis.

+3: Severe inflammation such as flare and swelling are locally observed with occurrence of substantial scales.

+4: Formation of thickened crust is observed.

Figure 2:
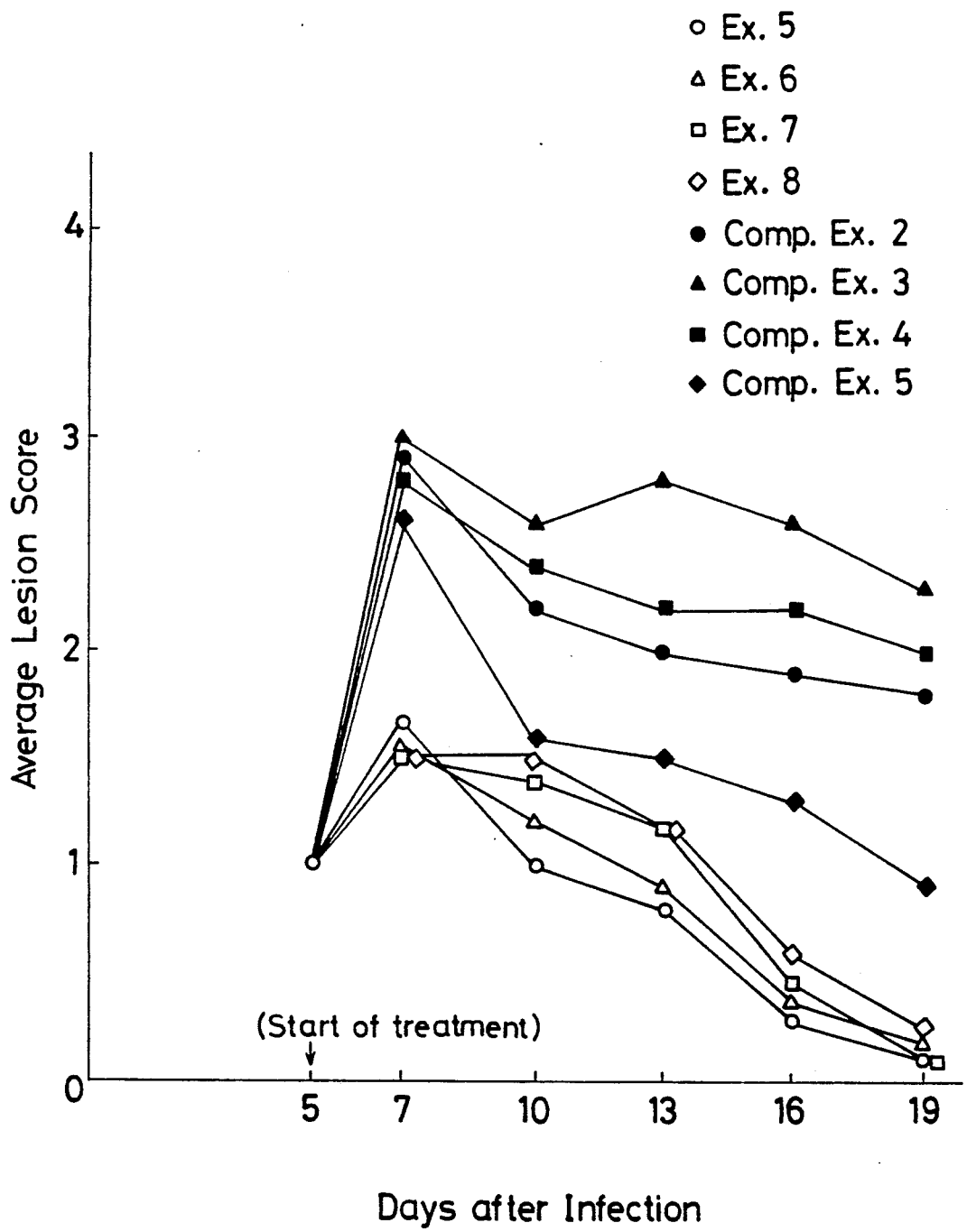
FIG. 2 diagrammatically depicts the results of the effectiveness test conducted in Test 1 with respect to the ointment preparations of the present invention, which shows their effectiveness in terms of average lesion score vs. days after infection.
Figure 3:
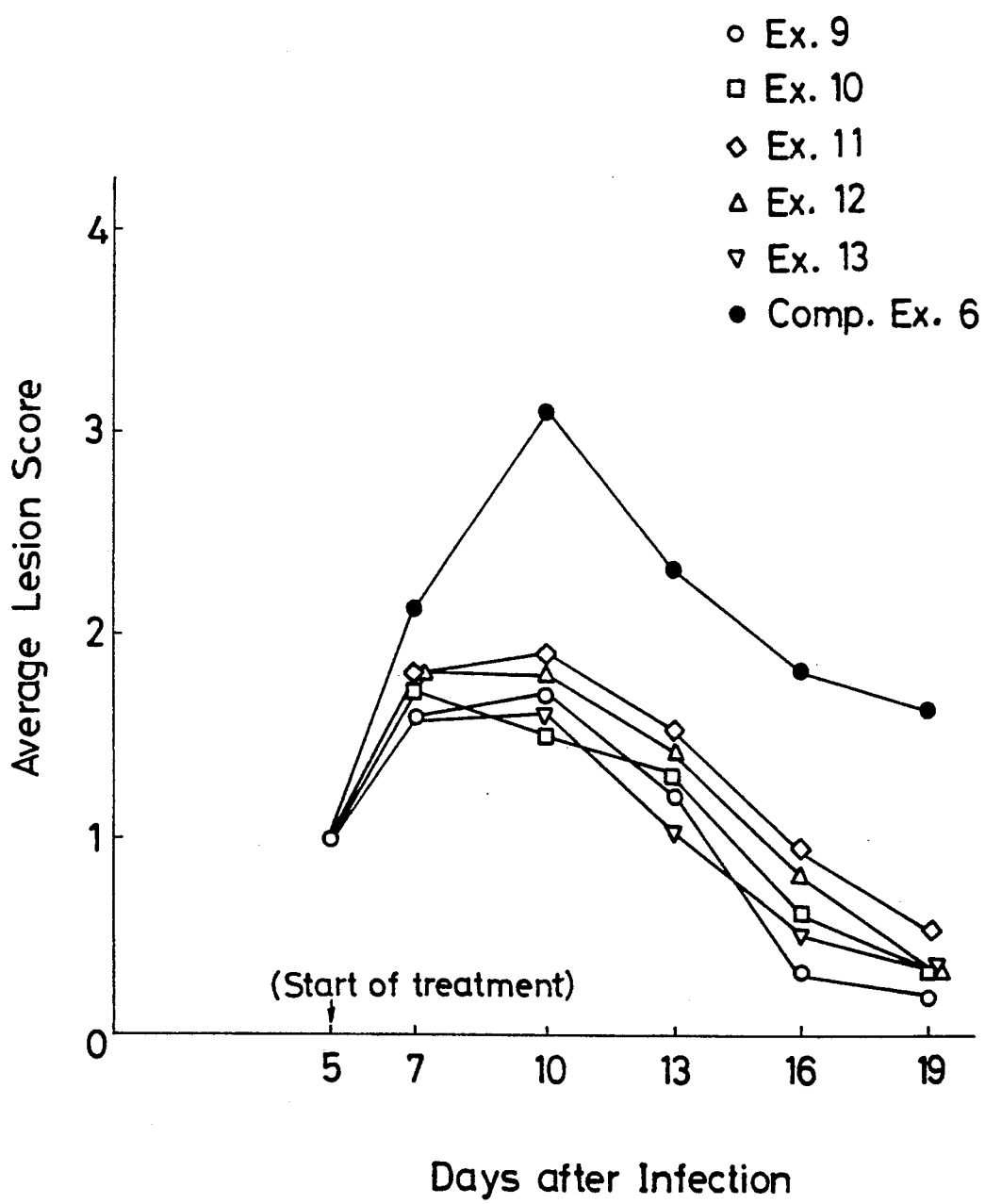
FIG. 3 diagrammatically illustrates the results of the effectiveness test conducted in Test 1 with respect to the cream preparations of the present invention, which shows their effectiveness in terms of average lesion score vs. days after infection.

The results of the above test are shown in FIG. 1 through FIG. 3.

As will become apparent from the respective figures, each of the external preparations of the present invention was recognized to have high effectiveness.

Test 2 (Safety Test)

A skin irritation test of certain external preparations according to this invention was conducted by the following method:

Pieces of a commercial patch test adhesive plaster (product of Torii & Co., Ltd.) were coated with the individual test preparations and were applied for 48 hours on a lower middle back area of each of 28-30 normal volunteers. Upon elapsed time of 1 hour and 24 hours after the removal of the adhesive plaster pieces, the degree of erythema (i.e., the degree of irritation to the skin) at the part coated with the preparation was determined.

Mild erythema and distinct erythema were indicated by ± and +, respectively. The degree of erythema was indicated by the percentage of erythema-bearing sections based on the entire area.

The results of the above test are summarized in Table 1 through Table 3.

TABLE 1

| | Determined 1 hour later | | Determined 24 hours later | Unit % |
|---|---|---|---|---|
| | ≧± | ≧+ | ≧± | ≧+ |
| Example 1 | 3.6 | 0 | 3.6 | 0 |
| Example 2 | 1.8 | 0 | 1.8 | 0 |
| Example 3 | 3.6 | 0 | 1.8 | 0 |
| Example 4 | 3.6 | 0 | 3.6 | 0 |

TABLE 1-continued

| | Determined 1 hour later | | Determined 24 hours later | Unit % |
|---|---|---|---|---|
| | ≧± | ≧+ | ≧± | ≧+ |
| Comp. Ex. 1 | 30.3 | 23.2 | 26.8 | 17.9 |

TABLE 2

| | 1 hour later | | 24 hours later | Unit % |
|---|---|---|---|---|
| | ≧± | ≧+ | ≧± | ≧+ |
| Example 5 | 0 | 0 | 0 | 0 |
| Example 6 | 0 | 0 | 0 | 0 |
| Example 7 | 0 | 0 | 0 | 0 |
| Example 8 | 1.7 | 0 | 0 | 0 |
| Comp. Ex. 2 | 3.3 | 0 | 0 | 0 |
| Comp. Ex. 3 | 5.0 | 0 | 1.7 | 0 |
| Comp. Ex. 4 | 3.3 | 0 | 0 | 0 |
| Comp. Ex. 5 | 10.0 | 1.7 | 3.3 | 0 |

TABLE 3

| | 1 hour later | | 24 hours later | Unit: % |
|---|---|---|---|---|
| | ≧± | ≧+ | ≧± | ≧+ |
| Example 9 | 0 | 0 | 0 | 0 |
| Example 10 | 3.6 | 0 | 0 | 0 |
| Example 11 | 7.1 | 0 | 3.6 | 0 |
| Example 12 | 0 | 0 | 0 | 0 |
| Example 13 | 0 | 0 | 0 | 0 |
| Comp. Ex. 6 | 19.6 | 8.9 | 8.9 | 5.4 |

As is envisaged clearly from each table, each of the external preparations of the present invention had extremely low skin irritation.

Test 3 (Stability Test)

A stability test of the external liquid preparations out of the external preparations according to this invention was conducted by the following method:

Each external liquid preparation was stored for 6 months in a constant-temperature chamber controlled at 40° C. and was tested for variations in external appearance and the content of the active ingredient (percent remainder). The results are summarized in Table 4.

TABLE 4

| Item tested Preparation | Variations in external appearance | Percent remainder (%) |
|---|---|---|
| Example 1 | − | 99.7 |
| Example 2 | − | 99.8 |
| Example 3 | − | 99.8 |
| Example 4 | − | 99.6 |
| Comp. Ex. 1 | + | 94.4 |

Variations in external appearance:
(−) No variation.
(+) Slight yellowing.

As is apparent from Table 4, the external liquid preparations of the present invention had excellent stability in both the physical properties and the active ingredient.

Test 4 (Stability Test)

A stability test of the ointment preparations out of the external preparations according to this invention was conducted by the following method:

Each ointment preparation was stored for 6 months in a constant-temperature chamber controlled at 40° C.

and was tested for discoloration, bleeding and the content of the active ingredient (percent remainder). The results are summarized in Table 5.

TABLE 5

| Item tested Preparation | Discoloration | Bleeding | Percent remainder (%) |
|---|---|---|---|
| Example 5 | − | − | 99.5 |
| Example 6 | − | − | 99.4 |
| Example 7 | − | − | 99.7 |
| Example 8 | − | − | 99.8 |
| Comp. Ex. 2 | + | − | 96.4 |
| Comp. Ex. 3 | − | − | 99.1 |
| Comp. Ex. 4 | + | − | 90.3 |
| Comp. Ex. 5 | + | + | 98.9 |

Discoloration: (−) no change, (+) slight yellowing.
Bleeding: (−) no bleeding, (+) slight bleeding.

As is clear from Table 5, the ointment preparations of the present invention underwent neither discoloration nor bleeding and the contents of the active ingredient remained substantially unchanged. They were hence recognized stable.

Test 5 (Stability Test)

A stability test of the cream preparations out of the external preparations according to this invention was conducted by the following method:

Each cream preparation was stored for 6 months in a constant-temperature chamber controlled at 45° C. and was tested for discoloration, separation and the content of the active ingredient (percent remainder). The results are summarized in Table 6.

TABLE 6

| Item tested Preparation | Discoloration | Separation | Percent remainder (%) |
|---|---|---|---|
| Example 9 | − | − | 99.8 |
| Example 10 | − | − | 99.6 |
| Example 11 | − | − | 99.6 |
| Example 12 | − | − | 99.0 |
| Example 13 | − | − | 99.4 |
| Comp. Ex. 6 | + | + | 95.7 |

Discoloration: (−) no change, (+) slight yellowing.
Separation: (−) no separation, (+) separated.

As is apparent from Table 6, the cream preparations of the present invention underwent neither discoloration nor separation and the contents of the active ingredient remained substantially unchanged. They were hence recognized stable.

We claim:

1. An antimycotic external imidazole preparation comprising the following ingredients:
   (a) 0.1–5 wt. % of (E)-1-[2-(pentyloxy)phenyl]ethenyl]-1H-imidazole hydrochloride;
   (b) 0.01–3 wt. % of a basic substance; and
   (c) an external preparation base; wherein said basic substance is selected from the group consisting of an organic amine and an inorganic alkali or a mixture thereof.

2. The preparation of claim 1, wherein the external preparation base, ingredient (c), contains 1–25 wt. % of a nonionic surfactant and 1–55 wt. % of a liquid oil substance and is in the preparation form of an external liquid preparation.

3. The preparation of claim 2, wherein the liquid oil substance is a saturated fatty acid ester.

4. The preparation of claim 2 or 3, wherein the nonionic surfactant is an ester-type nonionic surfactant between polyoxyethylene and a saturated fatty acid or an ether-type nonionic surfactant between polyoxyethylene and a saturated aliphatic alcohol.

5. The preparation of claim 1, wherein the external preparation base, ingredient (c), contains 2–5 wt. % of a nonionic surfactant and at least 80 wt. % of an oleaginous ointment base and is in the preparation form of an ointment preparation.

6. The preparation of claim 1, wherein the external preparation base, ingredient (c), contains 1–20 wt. % of a nonionic surfactant, 2–50 wt. % of an oil substance and 40–90 wt. % of water and is in the preparation form of a cream preparation.

7. The preparation of claim 1, wherein said basic substance is selected from the group consisting of monoalkylamine, dialkylamine, trialkylamine, monoalkanolamine, dialkanolamine, trialkanolamine, alkali hydroxide, and alkali carbonate or a mixture thereof.

* * * * *

UNITED STATES PATENT AND TRADEMARK OFFICE
CERTIFICATE OF CORRECTION

PATENT NO. : 5,100,908
DATED : March 31, 1992
INVENTOR(S) : Yutaka Murata, et al.

It is certified that error appears in the above-identified patent and that said Letters Patent is hereby corrected as shown below:

Column 12,
Lines 9-10, "(E)-1-[2-(pentyloxy)phenyl]ethenyl]-1H-imidazole hydrochloride" should read -- (E)-1-[2-methylthio-1-[2-(pentyloxy)phenyl]ethenyl]-1H-imidazole hydrochloride --.

Signed and Sealed this

Sixth Day of November, 2001

Attest:

NICHOLAS P. GODICI
Attesting Officer  Acting Director of the United States Patent and Trademark Office